United States Patent
Emmanuel

[11] Patent Number: 5,975,902
[45] Date of Patent: Nov. 2, 1999

[54] TOOTH SECUREMENT

[76] Inventor: E Mohan Emmanuel, "Greystones", Linton, United Kingdom, LS22 4JD

[21] Appl. No.: 08/676,133
[22] PCT Filed: Jan. 6, 1994
[86] PCT No.: PCT/GB94/00020
§ 371 Date: Sep. 25, 1996
§ 102(e) Date: Sep. 25, 1996
[87] PCT Pub. No.: WO94/15545
PCT Pub. Date: Jul. 21, 1994

[30] Foreign Application Priority Data
Jan. 7, 1993 [GB] United Kingdom ............... 9300221

[51] Int. Cl.⁶ ..................................................... A61C 8/00
[52] U.S. Cl. ............................................ 433/173; 433/172
[58] Field of Search ................................. 433/172, 173, 433/174, 175, 176

[56] References Cited

U.S. PATENT DOCUMENTS

| | | | |
|---|---|---|---|
| 2,112,007 | 3/1938 | Adams | 433/174 |
| 4,518,357 | 5/1985 | Brinkmann et al. | 433/173 |
| 4,713,003 | 12/1987 | Symington et al. | 433/173 |
| 4,907,969 | 3/1990 | Ward | 433/173 |
| 5,057,017 | 10/1991 | Sillard | 433/172 |
| 5,376,004 | 12/1994 | Mena | 433/174 |
| 5,460,526 | 10/1995 | Bosker | 433/172 |
| 5,520,540 | 5/1996 | Nardi et al. | 433/173 |

FOREIGN PATENT DOCUMENTS 1313597 2/1993 Canada.
0 216 031 4/1987 European Pat. Off..

OTHER PUBLICATIONS

Publication of corresponding PCT/GB94/00020 under WO 94/15545, Jul. 21, 1994.
International Preliminary Examination Report of PCT/GB94/00020, Mar. 24, 1995.
International Search Report of corresponding PCT/GB94/00020, May 18, 1994.

Primary Examiner—John J. Wilson
Attorney, Agent, or Firm—Woodard, Emhardt, Naughton, Moriarty & McNett

[57] ABSTRACT

A device for securing one or a plurality of teeth to the alveolar bone (60) of a patient is disclosed. The device includes osseointegratable parts (80), each of which has a screw-threaded fixture part (2a), an intermediate part (6a) and a head part (44a) which is generally dome-shaped A bridge (48) which may support one or a plurality of teeth is arranged to co-operate with the osseointegratable part (80) by means of dimples (52) in the bridge engaging respective head parts (44a), the bridge being secured in position by respective screws (62). As an alternative to a one-piece osseointegratablc part (80), an osseointegratable part which comprises three components is also described. A method of securing one or a plurality of teeth to the alveolar bone, a method of cosmetic treatment and a method of manufacturing parts of the device are also described.

14 Claims, 3 Drawing Sheets

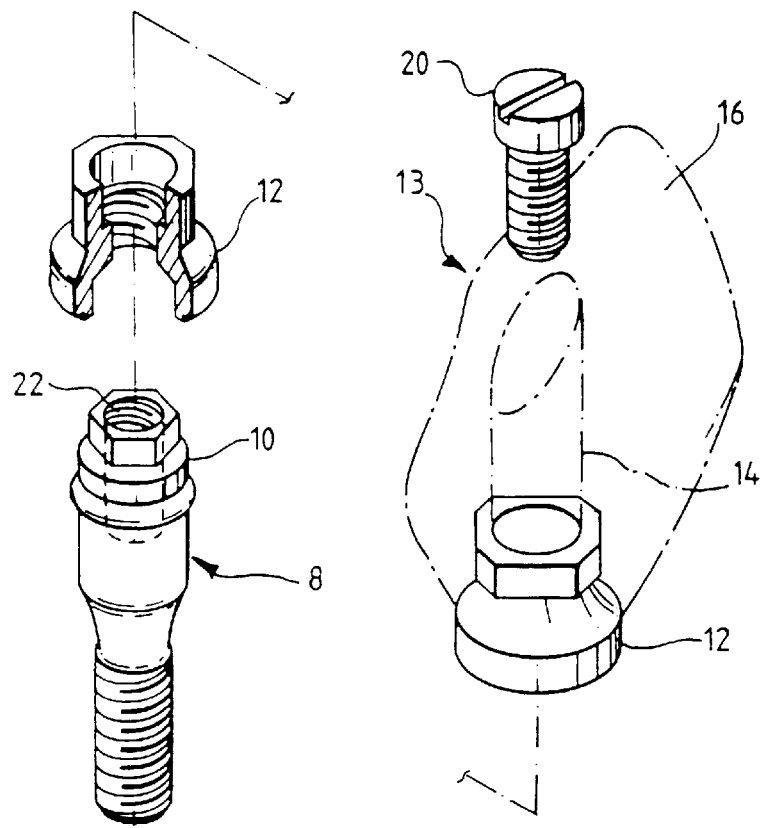
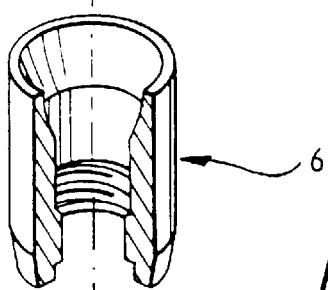
Fig.1.
(PRIOR ART)
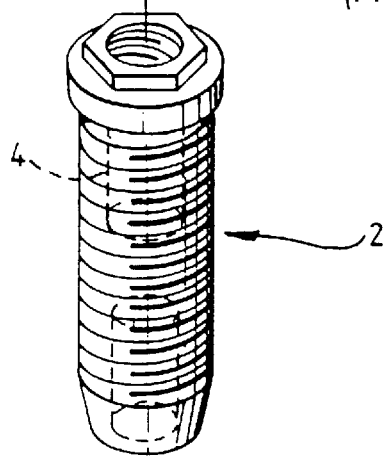

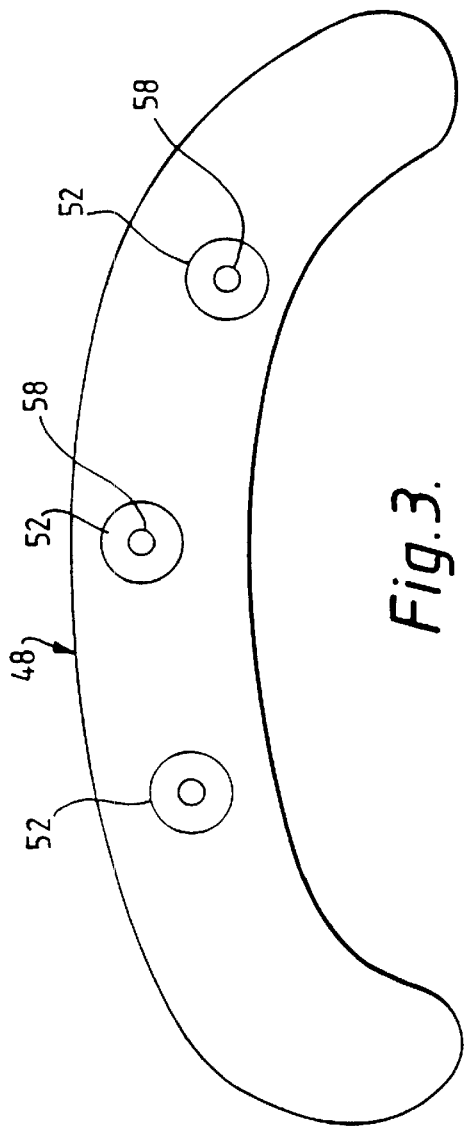
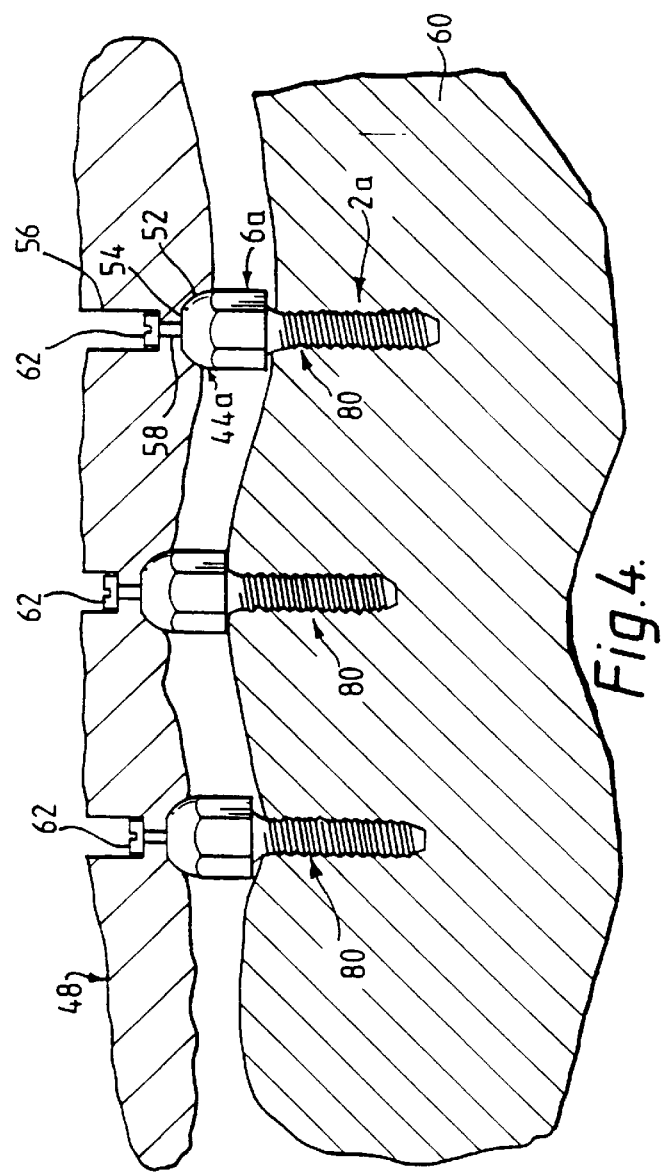

TOOTH SECUREMENT

FIELD OF THE INVENTION

This invention relates to the securement of one or a plurality of teeth and particularly, although not exclusively, to the securement of one or a plurality of teeth by means of an implant osseointegrated into the alveolar bone of a patient.

BACKGROUND OF THE INVENTION

It is well known to secure one or a plurality of teeth by means of an implant osseointegrated into the alveolar bone of a patient. One commercially available system, known as the Branemark System (Trade Mark), is shown in FIG. 1 of the accompanying diagrammatic drawings. Referring to FIG. 1, the system includes a titanium fixture 2 which is externally screw-threaded and which includes an inner channel 4 which is also screw-threaded. The fixture 2 is positioned within a threaded bore, formed in the alveolar bone, and allowed to osseointegrate over a period of about six months. In due course, an abutment sleeve 6 is positioned on the fixture 2 and secured thereon by means of an abutment screw 8. The abutment sleeve 6 extends through the mucosa above the alveolar bone and an upper part of the abutment screw 8 extends therefrom. The abutment screw 8 includes a tapered neck portion 10 which is arranged to provide a position of location for a correspondingly tapered portion of a gold cylinder 12. When assembled in a patient's mouth, an impression of the arrangement is taken and subsequently a prosthesis 13 which includes a gold framework 14 arranged to co-operate with the gold cylinder 12 and which carries an acrylic tooth 16 is made.

The prosthesis 13 may be positioned by locating the gold cylinder 12 and gold framework 14 upon the neck portion 10 of the abutment screw 8, and then securing the framework in position using a gold screw 20 which is received in internally threaded bore 22 of the abutment screw 8.

A problem associated with the use of the Branemark System as described above is that of the precise location of the tapered portion of the gold cylinder 12 (and tooth 16) with the tapered portion of the abutment screw 8, in order to ensure that any load upon the tooth 16, for example, during mastication, is equally distributed. This problem is particularly acute when a plurality of abutment screws 8 are located at spaced apart positions in the alveolar bone of a patient and wherein gold cylinders 12 are provided for co-operation with a single framework, carrying a plurality of teeth, and being arranged to extend between the abutment screws 8. It has been found in practice that, in many instances, there is an unequal distribution of loads on the abutment screws 8, leading to undue stresses upon specific regions of alveolar bone and also the loosening of the prosthesis. It is also noted that the use of components made of gold in the system described add significantly to the cost of such dental implants.

Dental implant devices have been proposed with a view to equally distributing loads upon the implant and providing an implant of lower cost. For example, U.S. Pat. No. 4,767,328 (Branemark) discloses a device for securing a plurality of teeth, comprising components 2, 4, 6, 8 and 10 described above. The device further includes a prefabricated rigid splint having an arc shape to fit the curve of the alveolar bone, and being attachable to a plurality of spaced apart abutment screws 8. An assembly comprising a plurality of false teeth is removably attached to the splint and the splint is arranged to function as a force distribution means during use. Optionally, a resilient member may be positioned between the assembly comprising the false teeth and the splint in order to further distribute the load. Nonetheless, with the device, it is still necessary to very precisely fabricate the splint for co-operation with the tapered portions of the abutment screws 8.

More recently, U.S. Pat. No. 5,057,017 (Sillard) has proposed a fixed removable dental implant system which includes components 2, 4, 6, 8 and 10 as described above and a precision cast bar securable to a plurality of abutment screws 8 by means of alloy screws. The construction of the precision cast support bar is accomplished using an impression of the patient's mouth from which a mould is made. The precision cast support structure is cast in a vacuum so as to reduce flaws thereof. Again, however, it is necessary to very precisely fabricate the support bar for co-operation with the tapered portions of the abutment screws 8.

It is an object of the present invention to alleviate some of the problems associated with known teeth securement systems.

SUMMARY OF THE INVENTION

According to a first aspect of the present invention, there is provided a device for securing one or a plurality of teeth to the alveolar bone, the device comprising first securement means securable to the alveolar bone such that a first axis of the first securement means is substantially upright, an outer part of the first securement means including a curved surface which curves towards the first axis, the device further comprising a tooth securement member which is co-operable with the outer part for securing one or a plurality of teeth to the alveolar bone.

The device of the present invention may provide advantages over the device used in the Branemark system described above, since that system relies on the passive fit of tapering surfaces which surfaces are circumferentially disposed about an elongate axis of the device.

The first securement means of the first aspect is preferably arranged to be screwed into the alveolar bone. To this end, the first securement means suitably includes a screw-threaded region at or towards an inner end thereof. The screw-threads of the screw-threaded region are preferably arranged about the first axis; that is, the rotational axis of the screw-threaded region is preferably coincident with the first axis. The first securement means is preferably arranged to become osseointegrated into the alveolar bone. To this end, the first securement means is preferably made of titanium, at least in a region thereof which is positioned in use within the alveolar bone. The whole of the first securement means may be made of titanium.

The first securement means preferably includes a mucosal part which is arranged to extend through the mucosa above the alveolar bone. The outer part of the first securement means is preferably arranged to extend above the mucosa.

The outer part of the first securement means is preferably symmetrically arranged about the first axis. The outer part may include a single continuous curved surface or may include a plurality of spaced apart curved surfaces. Preferably, the outer part includes a continuous curved surface which extends circumferentially about the first axis. The curved surface is preferably partially spherical, with the centre of the sphere preferably being disposed on the first axis. The curved surface is preferably substantially hemispherical. The outer part may include a substantially planar region which is preferably circular in cross-section and which is preferably axially aligned with the first axis. The substantially planar region may interrupt, in part, the curved surface of the outer part. For example, where the curved surface is partially spherical, for example, substantially hemispherical, the substantially planar region may interrupt the spherical surface.

Preferably, the curved surface of the outer part is a convex surface.

In a preferred embodiment, the outer part of the first securement means is substantially dome-shaped. The dome may have a parabolic, for example part-circular, cross-section. The dome may include a substantially planar region which interrupts its outer surface. The planar region may be as described above.

The tooth securement member preferably includes a curved surface which substantially corresponds in shape to that of the curved surface of the outer part. The tooth securement member is preferably arranged to be engaged closely with the curved surface of the outer part. When the curved surface of the outer part is convex, preferably the curved surface of the tooth securement member is concave. In a preferred embodiment, the curved surface of the tooth securement member is partially spherical, more preferably substantially hemispherical.

The device suitably includes second securement means for securing the first securement means to the tooth securement member. The second securement means preferably includes a screw-threaded socket arranged to be engaged by a screw. Preferably, the screw-threaded socket is provided in the first securement means. In this case, preferably, the screw-threaded socket is aligned with the first axis. The screw-threaded socket preferably opens through the outer part of the first securement means. Said tooth securement member is preferably arranged to co-operate with a screw engagable in the screw-threaded socket. For example, the tooth securement member preferably includes a bore arranged to receive the screw and being axially alignable with the screw-threaded socket of the first securement means.

The outer part of the first securement means is preferably fixed in position relative to inner parts thereof. The curved surface of the outer part preferably extends in a pre-defined, unadjustable direction relative to the first axis.

The first securement means preferably comprises a plurality of parts which are attachable to one another. In a preferred embodiment, the first securement means includes a first part which is arranged to be screwed into the alveolar bone as described above and a separate second part which includes the outer part. The first and second parts are preferably arranged to be screwed together.

Preferably, the first securement means comprises only three parts—the first and second parts as described above and a third part arranged to be positioned between the first and second parts.

In another embodiment, the first securement means may comprise a single part which is arranged to be secured to the alveolar bone as described above and which includes an outer part as described above.

The device may include a plurality of the first securement means described above. Each of the securement means is preferably arranged to co-operate with said tooth securement member. The tooth securement member may include one or a plurality of teeth attached thereto.

Where a single first securement means is provided for co-operation with a tooth securement member, preferably means is provided for restricting rotation of the first securement means relative to the tooth securement member.

According to a second aspect of the present invention, there is provided a first securement means as described in any statement herein, the first securement means being securable to the alveolar bone such that a first axis of the first securement means is substantially upright, an outer part of the first securement means including a curved surface which curves towards said first axis and the outer part being arranged to co-operate with a tooth securement member for securing one or a plurality of teeth to the alveolar bone.

According to a third aspect of the present invention, there is provided a securement part, for example, a securement screw, for a device for securing one or a plurality of teeth to the alveolar bone as described in any statement herein, the securement part having a first axis and being arranged to co-operate with an osseointegrated part, for example, a screw-threaded socket osseointegrated in the alveolar bone so that the first axis is substantially upright, an outer part of the securement part including a curved surface which curves towards said first axis and is arranged to co-operate with a tooth securement member for securing one or a plurality of teeth to the alveolar bone.

According to a fourth aspect of the present invention, there is provided a method of securing one or a plurality of teeth to the alveolar bone, the method using a device according to the first aspect and comprising securing the first securement means to the alveolar bone and securing the tooth securement member to the first securement means.

The invention extends to a method of cosmetic treatment using a device according to the first aspect, the method comprising securing the first securement means to the alveolar bone and securing the tooth securement member to the first securement means.

The invention further extends to a method of manufacturing a tooth securement member for co-operation with first securement means as described herein, the method comprising assessing the characteristics and/or position of the first securement means when secured to the alveolar bone and using the assessment to control the production, for example, by machining, of the tooth securement member from a blank, for example, a wrought blank of, for example, titanium or cobalt chrome.

BRIEF DESCRIPTION OF THE DRAWINGS AND DESCRIPTION OF PREFERRED EMBODIMENTS

Specific embodiments of the present invention will now be described, by way of example, with reference to the accompanying diagrammatic drawings, in which:

FIG. 1 is an exploded view showing components of the Branemark System (Trade Mark) described above;

FIG. 3 is an underneath plan view of a bridge of the device of the present invention; and FIG. 4 is a vertical cross-section through the alveolar bone of a patient showing a device of the present invention in situ.

Some of the components of the device of the present invention are the same or similar to those utilised in the Branemark system as described with reference to FIG. 1. In the figures the same or similar parts have the same reference numerals.

Figure 2:
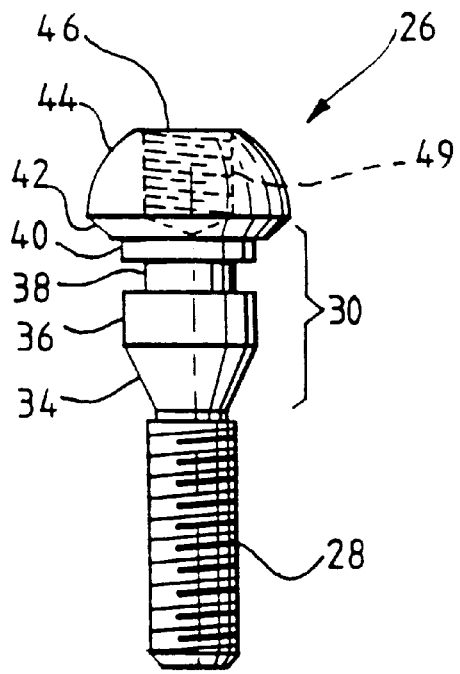
FIG. 2 is an exploded view of components of a device of the present invention, with portions of the components being shown in cross-section.
Figure 2:
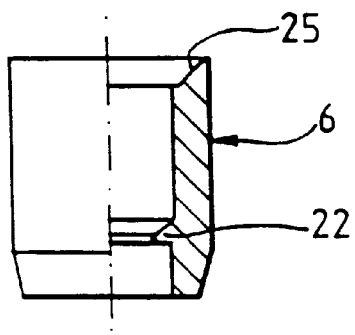
Figure 2:
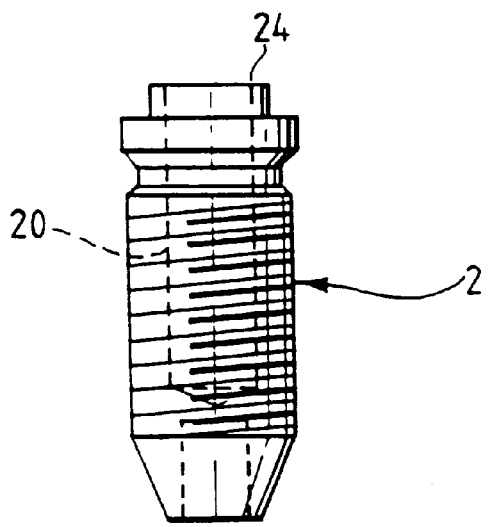

Referring to FIG. 2, there is shown a titanium fixture 2 arranged to be positioned within the alveolar bone and become osseointegrated therewith. As described above, the fixture 2 is externally screw-threaded, to aid securement within the bone, and also includes an internally screw-threaded axially extending bore 20. The fixture 2 is arranged to co-operate with an abutment sleeve 6. The abutment sleeve 6 includes a radially extending annular shoulder 22, the lower surface of which is arranged to abut an upper surface 24 of the fixture 2 when the sleeve 6 is positioned thereupon. At its upper end, the sleeve 6 includes a tapering annular seat 25, wherein the. angle of taper is about 45°. The tapering annular seat is arranged to provide a seat for location of an abutment screw 26.

The abutment screw 26 includes, towards its lower end, an externally screw-threaded shaft portion 28. The shaft portion 28 is connected to a neck portion 30 which comprises a frusto-conical portion 34, a first wide diameter cylindrical portion 36, a narrow diameter cylindrical portion 38, a second wide diameter cylindrical portion 40 and a tapering portion 42. The tapering portion 42 is arranged to abut the tapering annular seat 25 of the sleeve 6, to locate the abutment screw 26 in position.

The annular portion 42 is connected to a dome-shaped head 44. The head 44 includes a substantially hemispherical part and a flattened region 46 which is substantially circular in plan view and is axially aligned with the hemispherical part. An internally threaded axially extending bore 49 is provided in the head 44. The head 44 is arranged to co-operate with bridge 48 (FIG. 3) for securing a plurality of false teeth in position.

Referring to FIG. 3, the bridge 48 is arcuate in shape and arranged to follow the shape of the alveolar bone 60. The bridge carries a plurality of false teeth (not shown) thereon. On its lower side, shown in the Figure, the bridge includes three spaced-apart dimples 50 each of which is arranged to co-operate with a head 44 of an abutment screw 26. Thus, the dimples include a substantially hemispherical part 52 and a flattened region 54 (FIG. 4). Relatively wide cylinder-shaped bores 56, which are open to the upper side of the bridge 48, communicate with relatively narrow cylinder-shaped bores 58 which, in turn, open into the dimples 50, via the flattened region 54.

With the fixtures 2 osseointegrated in the alveolar bone 60 and the sleeves 6 and abutment screws 26 securely fixed in position, the bridge 48 is positioned with its dimples 52 overlying and abutting the heads 44 of the screws 26. Then, screws 62 are inserted into the bores 56 and screwed into the bores 20 in the heads 44 of the abutment screws 26, so as to secure the bridge 48 in position.

In FIG. 4, a one-piece osseointegratable part 80 is shown. The part 80 includes a fixture part 2a which corresponds to the fixture 2 of FIG. 2, an intermediate part 6a which corresponds to the abutment sleeve 6 of FIG. 2 and a head part 44a which corresponds to the head 44 of the abutment screw 26. The bridge co-operates with the osseointegratable part 80 as described above and as shown in FIG. 4.

It should be appreciated that one or a plurality of co-operating dome-shaped heads and dimples may be provided depending upon the number of false teeth carried by a bridge. A bridge may, for example, include only a single dimple when only one false tooth is to be fitted. In this case, a means is provided for restricting rotation of the head relative to the bridge.

The manufacture of components of the device described above and the fitment of false teeth to a patient are now described in greater detail.

Fixture 2, abutment sleeve 6 and abutment screw 26 are manufactured by standard techniques. In use, the fixture 2 is allowed to become osseointegrated into the alveolar bone 60 prior to the securement thereto of the sleeve 6 and the screw 26. If the one-piece osseointegratable part 80 is used, this is allowed to become osseointegrated. Then, an impression is taken of the patient's mouth by standard techniques, so as to clearly show the arrangement of the heads 44 or 44a. From this impression, the bridge 48 is made by casting or by machining. It has been found that the bridge can satisfactorily be made from titanium by the aforementioned methods. A preferred method of making the bridge involves using a probe to map out exactly the characteristics of the impression (e.g. the relative positions of the dimples), storing the characteristics in a computer and then using the computer to control the machining of a wrought titanium beam according to the characteristics required. A 3 axis CNC co-ordinate measuring machine with full 3D digitising software and a PH 9 type motorised probe head is used. This is coupled to a post processor which can convert the information into co-ordinates compatible with either a 3/5 axis CNC machining centre or EDM.

Once the bridge has been made, the false teeth may be fixed thereto by known techniques.

Once completed, the bridge 48 may be permanently secured in position by using screws 62 as described above.

It has been found that the provision of bridge 48 and abutments screws 26 described herein allow securement of false teeth in an advantageous manner.

The location of the bridge 48 on the abutment screws 26 has been found to be more precise than in, for example, the arrangement of the FIG. 1 embodiment. This may, therefore, provide a more even distribution of loads and greater comfort for a patient. Since the bridge 48 may be machined from a wrought titanium beam (rather than being cast using a gold alloy) this may increase the strength and durability of the device for a reduced cost. As an alternative to the use of a wrought titanium beam, a cobalt chrome beam may be used.

As an alternative to the use of a three component stack comprising a fixture 2, sleeve 6 and abutment screw 26, or the one-piece osseointegratable part 80, a two component stack may be provided which utilises a fixture 2 as described above in combination with a second part in which sleeve 6 and screw 26 are formed as a single part.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

I claim:

1. A device for securing one or a plurality of teeth to the alveolar bone, the device comprising a plurality of first securement means securable to the alveolar bone such that respective first axes of said first securement means are substantially upright, an outer part of each first securement means including a respective curved surface which curves towards a respective first axis, the device further comprising a tooth securement member which includes respective curved surfaces which substantially corresponds in shape to that of respective curved surfaces of said outer parts and are co-operable with respective said outer parts for securing a plurality of teeth to the alveolar bone, wherein said first securement means include screw-threaded socket for engagement by screws in order to secure the tooth securement member against movement away from said first securement means.

2. A device according to claim 1, wherein said first securement means are arranged to be screwed into the alveolar bone.

3. A device according to claim 1, wherein each of said first securement means includes a mucosal part which is arranged to extend through the mucosa above the alveolar bone.

4. A device according claim 1, wherein each outer part of the first securement means is arranged to extend above the mucosa.

5. A device according to claim 1, wherein each outer part of the first securement means is symmetrically arranged about a respective first axis.

6. A device according to claim 1, wherein each outer part of the first securement means includes a continuous curved surface which extends circumferentially about a said respective first axis.

7. A device according to claim 1, wherein each said curved surface of said outer parts of said first securement means is partially spherical, with the center of the sphere being disposed on said respective first axis.

8. A device according to claim 1, wherein each said curved surface of said outer parts of said first securement means is convex.

9. A device according to claim 1, wherein said tooth securement member includes respective concave surfaces for with said outer parts of the first securement means.

10. A device according to claim 1, wherein each said screw-threaded socket opens through a said outer part of a respective said first securement means.

11. A device according to claim 1, wherein each said outer part of a said first securement means is fixed in position relative to inner parts thereof.

12. A device according to claim 1, wherein each said curved surface of said outer parts of said first securement means extends in a predefined, unadjustable direction relative to a said respective first axis.

13. A method of securing one or a plurality of teeth to the alveolar bone, the method using a device according to claim 1 and comprising securing a plurality of said first securement means to the alveolar bone and securing said tooth securement member to each of said first securement means by engaging respective screws in each said screw-threaded socket provided in said first securement means.

14. A device for securing a plurality of teeth to the alveolar bone, the device comprising a plurality of first securement means secured to the alveolar bone such that respective first axes of said first securement means are substantially upright, an outer part of each first securement means including a respective curved surface which curves towards a said respective first axis, the device further comprising a tooth securement member which includes respective curved surfaces which substantially correspond in shape to that of respective curved surfaces of said outer parts and are co-operable with said outer parts for securing a plurality of teeth to the alveolar bone, wherein said first securement means include screw-threaded sockets for engagement by respective screws in order to secure the tooth securement member against movement away from said first securement means.

* * * * *